(12) United States Patent
Sturge

(10) Patent No.: US 12,251,485 B2
(45) Date of Patent: Mar. 18, 2025

(54) AEROSOLIZED NON-TOXIC DISINFECTANT ATMOSPHERICS SYSTEM

(71) Applicant: Thomas Graham Sturge, Maple Valley, WA (US)

(72) Inventor: Thomas Graham Sturge, Maple Valley, WA (US)

(*) Notice: Subject to any disclaimer, the term of this patent is extended or adjusted under 35 U.S.C. 154(b) by 682 days.

(21) Appl. No.: 17/647,520

(22) Filed: Jan. 10, 2022

(65) Prior Publication Data

US 2022/0218858 A1 Jul. 14, 2022

Related U.S. Application Data

(60) Provisional application No. 63/199,555, filed on Jan. 8, 2021.

(51) Int. Cl.
| | | |
|---|---|---|
| *A61L 2/22* | (2006.01) | |
| *A01N 25/06* | (2006.01) | |
| *A01N 25/30* | (2006.01) | |
| *A01N 37/36* | (2006.01) | |
| *A01N 59/00* | (2006.01) | |
| *A01P 1/00* | (2006.01) | |
| *A61L 2/26* | (2006.01) | |

(Continued)

(52) U.S. Cl.
CPC .............. *A61L 2/22* (2013.01); *A01N 25/06* (2013.01); *A01N 25/30* (2013.01); *A01N 37/36* (2013.01); *A01N 59/00* (2013.01); *A01P 1/00* (2021.08); *A61L 2/26* (2013.01); *A61L 9/14* (2013.01); *C09K 3/24* (2013.01); *A61L 2101/36* (2020.08); *A61L 2101/40* (2020.08); *A61L 2202/14* (2013.01); *A61L 2202/15* (2013.01); *A61L 2202/25* (2013.01); *A61L 2209/111* (2013.01); *A61L 2209/134* (2013.01); *A61L 2209/15* (2013.01); *A61L 2209/211* (2013.01)

(58) Field of Classification Search
CPC ................ A01P 1/00; C09K 3/00; C09K 3/24
See application file for complete search history.

(56) References Cited

U.S. PATENT DOCUMENTS

| | | |
|---|---|---|
| 6,491,231 B1 | 12/2002 | Eliasson et al. |
| 7,097,717 B2 | 8/2006 | Jung et al. |

(Continued)

*Primary Examiner* — Natasha E Young
(74) *Attorney, Agent, or Firm* — Dunlap Bennett & Ludwig, PLLC; Anna L. Kinney

(57) ABSTRACT

A modular anti-microbial aerosol atmospheric effect delivery system includes an air compressor, a haze solution reservoir, and an artificial snow solution reservoir in a system enclosure and an electronically controlled haze module and artificial snow module mounted above an attendee room. The haze module is connected to the air compressor and the haze solution reservoir by a hose system. The artificial snow module fluidly is connected to the air compressor and the artificial snow solution reservoir by the hose system. The artificial snow solution reservoir contains an artificial snow solution including sodium lauryl sulfate and citric acid. The haze solution reservoir contains a haze solution propylene glycol or tri-ethylene glycol, and at least one anti-microbial component selected from hydrogen peroxide and citric acid. The solutions are safe and antivirally effective to kill aerosol microbes suspended in the air, reducing transmission of undesirable microbes amongst attendees and workers within indoor environments.

10 Claims, 3 Drawing Sheets

(51) Int. Cl.
  *A61L 9/14*      (2006.01)
  *A61L 101/36*    (2006.01)
  *A61L 101/40*    (2006.01)
  *C09K 3/24*      (2006.01)

(56) References Cited

U.S. PATENT DOCUMENTS

| | | |
|---|---|---|
| 7,462,590 B2 | 12/2008 | Tichy et al. |
| 8,715,586 B2 | 5/2014 | Park et al. |
| 9,238,239 B2 * | 1/2016 | Adams ................. B05B 7/0416 |
| 9,803,906 B2 * | 10/2017 | Ko ........................... F25C 1/10 |
| 10,377,557 B1 | 8/2019 | Edmond |
| 10,391,188 B2 | 8/2019 | Shane et al. |
| 10,507,256 B2 | 12/2019 | Park et al. |
| 2005/0282722 A1 * | 12/2005 | McReynolds ........ C11D 3/3947 |
| | | 510/302 |
| 2006/0078461 A1 | 4/2006 | Kaplan |
| 2007/0053188 A1 | 3/2007 | New et al. |
| 2008/0089817 A1 | 4/2008 | Cacciabaudo |
| 2011/0044849 A1 | 2/2011 | Infiesta et al. |
| 2012/0275952 A1 | 11/2012 | Lukasik et al. |
| 2015/0258233 A1 | 9/2015 | Brown et al. |
| 2016/0095947 A1 | 4/2016 | Malaguti Simoni et al. |
| 2016/0166723 A1 | 6/2016 | Kachouh |
| 2018/0353632 A1 | 12/2018 | Divisi |
| 2019/0167829 A1 | 6/2019 | Grinstead |
| 2019/0275185 A1 | 9/2019 | Sakaki |

\* cited by examiner

AEROSOLIZED NON-TOXIC DISINFECTANT ATMOSPHERICS SYSTEM

CROSS-REFERENCE TO RELATED APPLICATION

This application claims the benefit of priority of U.S. provisional application No. 63/199,555, filed Jan. 8, 2021, the contents of which are herein incorporated by reference.

BACKGROUND OF THE INVENTION

The present invention relates to a system for generating atmospherics, such as artificial "haze" and "snow", and, more particularly, to a system employing non-toxic aerosolized disinfectants, as well as to compositions therefor.

Humans are vulnerable to harmful microbes and airborne pathogens such as the novel coronavirus in enclosed spaces. The resulting infections from indoor exposure have impacted countless aspects of life worldwide. The ability to provide a non-toxic disinfected indoor atmosphere will continue to be a relevant safety measure well beyond the current coronavirus pandemic. We may see a requirement for safe and disinfected atmospheric environments for many indoor live events in the near future.

Current technology uses ultraviolet (UV) light to "cleanse" the air and then recirculate this air back into the occupied space. In the event industry the use of currently available technologies produces visual effects of "haze" and "artificial snow" to enhance the lighting and visual impact in the concert, theater, and other live event industries. Current event-specific atmospheric delivery systems do not address aerosolized pathogens and are solely intended for visual appeal. Moreover, current systems create unacceptably high sound levels and are unusable in many spaces.

Current technology uses standalone devices to create "haze" using compressed air and mineral oil, tri-ethylene glycol, and/or propylene glycol. "Snow" is created using forced air and various soap solutions. Currently, neither of these systems address the need for disinfection. Current disinfectant protocols are based on surface treatments, which while necessary does not address aerosol viral transmission between humans.

As can be seen, there is a need for a safe and effective system to disinfect the atmosphere of indoor spaces used for live events, as well as disinfection compositions for use with the system.

SUMMARY OF THE INVENTION

In one aspect of the present invention, a modular anti-microbial aerosol atmospheric effect delivery system is provided, comprising: an air compressor in a system enclosure; a haze solution reservoir in the system enclosure; an artificial snow solution reservoir in the system enclosure; an electronically controlled haze module mounted above an attendee room; and an electronically controlled artificial snow module mounted above the attendee room; wherein said electronically controlled haze module fluidly communicates with the air compressor and the haze solution reservoir by way of a hose system and said electronically controlled artificial snow module fluidly communicates with the air compressor and the artificial snow solution reservoir by way of the hose system. The inventive system is an improvement on prior art standalone devices.

In another aspect of the present invention, aerosol anti-microbial atmospheric effect compositions are provided, comprising: an artificial snow solution comprising sodium lauryl sulfate and citric acid; and a haze solution comprising propylene glycol or tri-ethylene glycol, and at least one anti-microbial component selected from the group consisting of hydrogen peroxide and citric acid. The inventive system is an improvement on the prior art by the addition of citric acid and/or hydrogen peroxide to the compositions as an anti-microbial element.

In yet another aspect of the present invention, an atmospheric effect delivery method of disinfecting an inhabited room is provided, comprising: providing the modular anti-microbial aerosol atmospheric effect delivery system; providing the artificial snow solution and the haze solution; delivering the haze solution and compressed air to the electronically controlled haze module; delivering the artificial snow solution and the compressed air to the electronically controlled artificial snow module; continuously operating the electronically controlled haze module; and intermittently operating the electronically controlled artificial snow module. The inventive system may interface with existing industry control devices.

These and other features, aspects and advantages of the present invention will become better understood with reference to the following drawings, description, and claims.

DETAILED DESCRIPTION OF THE INVENTION

Figure 1:
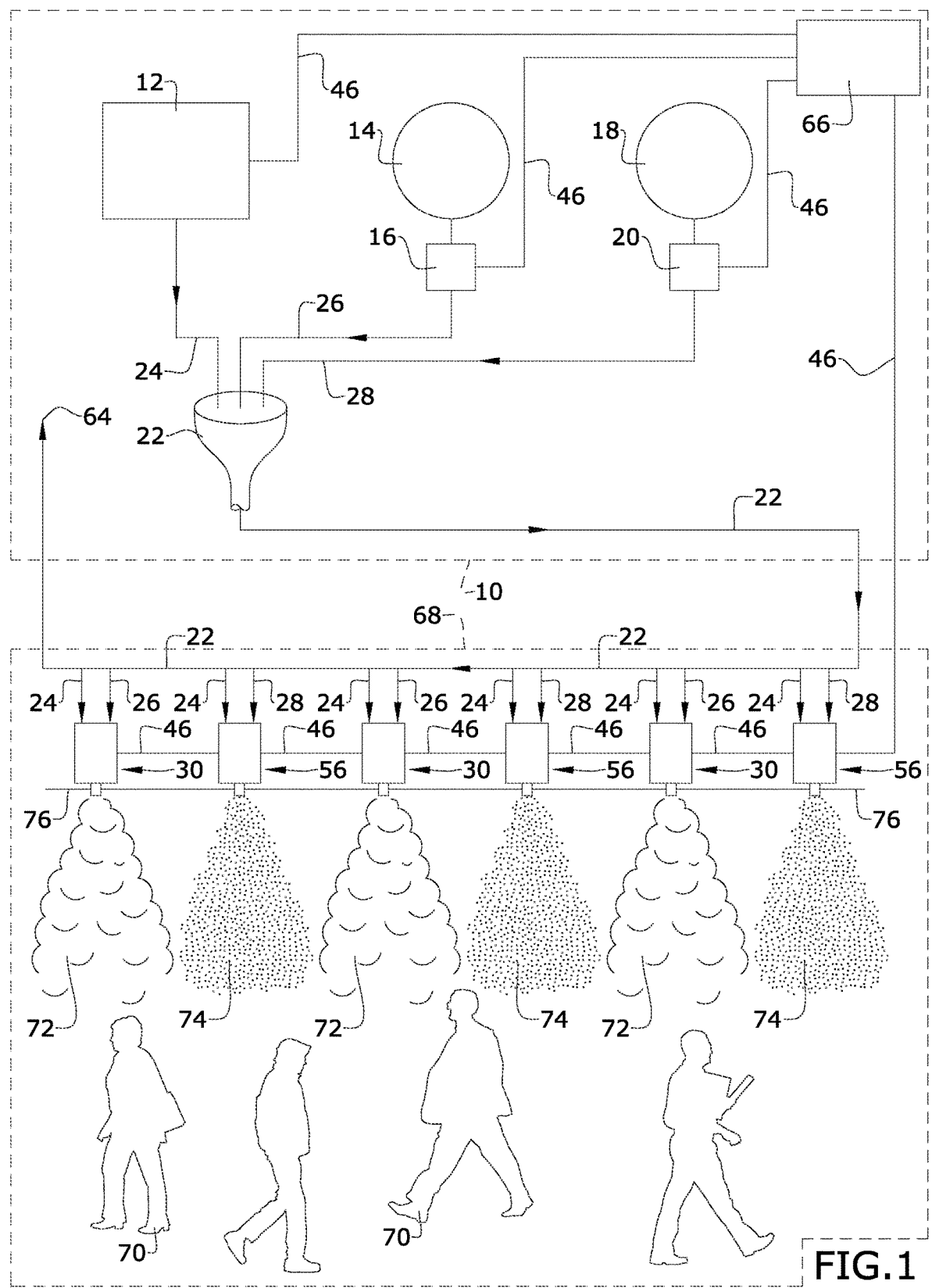
FIG. 1 is a schematic view of an atmospherics system according to an embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is safe and effective anti-microbial liquid solutions and a modular aerosol delivery system therefor.

The anti-microbial liquid solutions and delivery system provide a safe and antivirally effective aerosolized "haze" or "snow" solution comprising a mixture of components selected from the group consisting of: citric acid, propylene glycol, tri-ethylene glycol, hydrogen peroxide, and sodium lauryl sulfate. The inventive solution may kill aerosol microbes suspended in the air, reducing transmission of undesirable microbes, including the severe acute respiratory syndrome coronavirus 2 (SARS-CoV-2), amongst attendees and workers at live events and other indoor activities. The inventive modular delivery system distributes the anti-viral solution safely and evenly throughout the atmosphere of enclosed spaces, and may improve the disinfection capabilities of prior art techniques using ultraviolet light disinfection, increased ventilation, and more robust air filtration. The unified system preferably provides safe, effective, and quiet aerosolized non-toxic atmospheric anti-microbial protection. The inventive system may produce a safe indoor environment for human group activities such as, but not limited to, concerts, corporate tradeshows, live theater, events within houses of worship, bars, restaurants, nightclubs, etc. Moreover, the system may be more robust, quieter, more expandable, and more efficient than currently available delivery systems.

The invention adds non-toxic anti-viral and anti-microbial properties to commonly used atmospheric effects which may significantly lower microbial transmission and facilitate a full restart of group activities.

In some embodiments, the inventive liquid solutions may be used in existing distribution systems, especially where noise is not a problem such as concerts, clubs, and bars. "Haze" may be generated by aerosolizing, with compressed air, a non-toxic liquid solution comprising at least one alkene glycol selected from the group consisting of propylene glycol and tri-ethylene glycol, and at least one anti-microbial component selected from the group consisting of hydrogen peroxide and citric acid. "Snow" may be generated by blowing air through a non-toxic liquid solution comprising sodium lauryl sulfate and citric acid. Preferably, both the "haze" and the "snow" compositions evaporate and do not leave unwanted residue or create other hazardous conditions. In some cases, the inventive compositions provide additional surface disinfection.

The compositions and relative amounts of the components thereof are not particularly limited, provided that they achieve anti-viral efficacy and personal exposure safety. For example, the compositions may avoid eye/nose/throat and skin irritation factors while achieving anti-microbial efficacy determined by testing. Preferably, all compounds employed thereof are classified as Generally Recognized As Safe (GRAS) by the United States Food and Drug Administration (USFDA). Preferably, disinfectant components are included in the United States Environmental Protection Agency (USEPA) List N: Disinfectants for Coronavirus (Covid 19). Preferably, the "haze" and/or "snow" compositions may be tested in a controlled environment using standard scientific practice and then may be tested in "real world" settings in accordance with local laws and regulations. A commercial manufacturing process may be developed prior to marketing the liquid solutions.

The inventive modular delivery system comprises remote air compressors, solution reservoirs, hose systems for compressed air and solution distribution, and electronically controlled "haze" and "snow" modules installed either permanently in the ceiling area or temporarily attached to rigged truss and/or superstructure above the spaces to be disinfected. The inventive distribution system may provide better atmospheric coverage, control, maintenance, and noise mitigation than currently available standalone products and may allow use in a wide range of indoor environments. The modular nature of the proposed system preferably allows for expandability and adaptability, i.e., a buildable distribution system. For example, in some cases, a single "haze" module may be sufficient to achieve the anti-microbial properties and reduce infection risk in enclosed spaces. In other cases, multiple modules may be preferred.

The inventive modular distribution system comprising air compressors and hosing systems improves on currently available distribution systems. Generally, the "haze" modules may run substantially continuously to provide a constant anti-microbial, safe, and breathable atmosphere while the "snow" modules may run intermittently to cleanse the air and surfaces that the aerosolized sodium lauryl sulfate/citric acid mixture encounters. The inventive system may be controlled by industry control desks and protocols known in the art.

Figure 2:
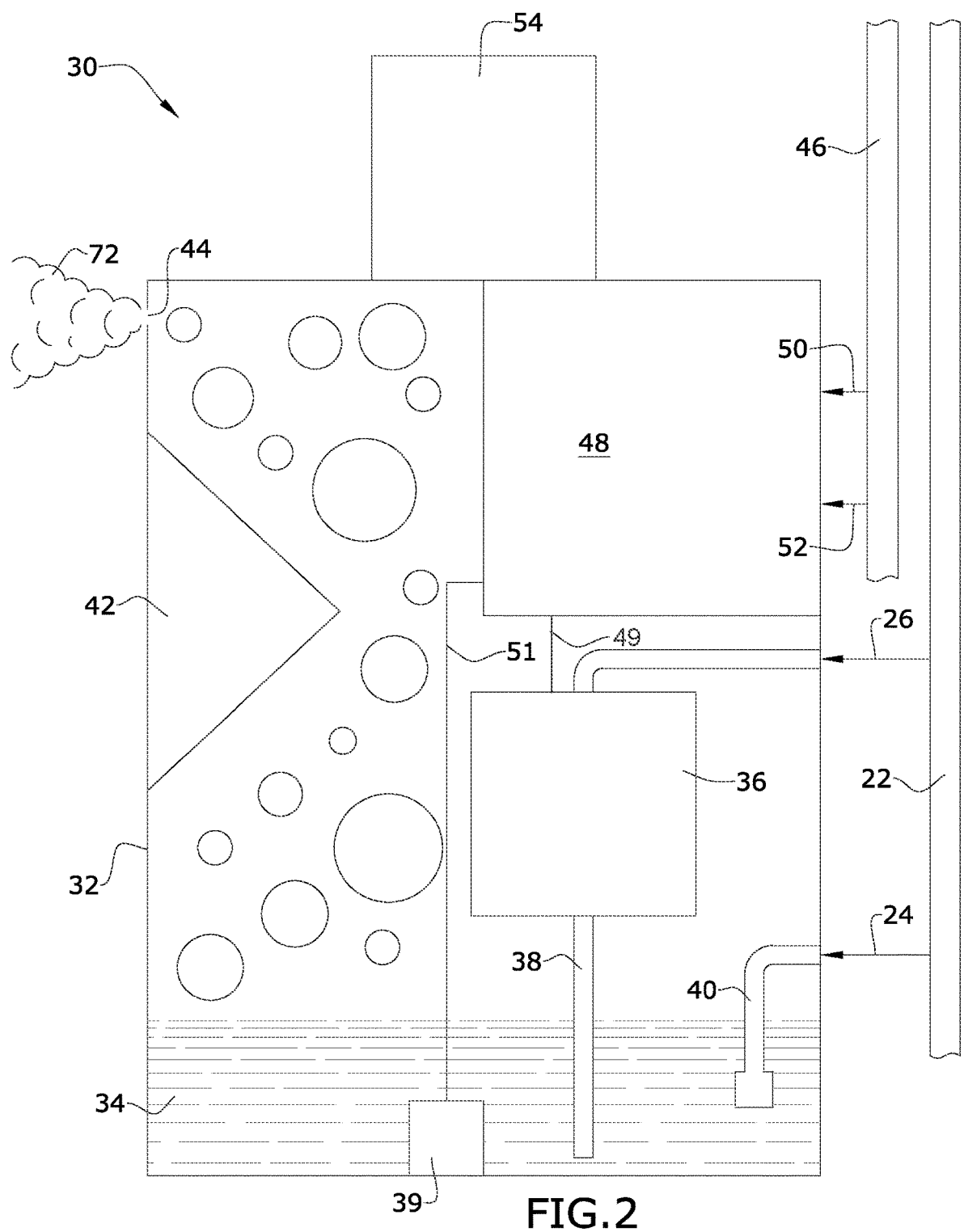
FIG. 2 is a schematic view of a haze module thereof.
Figure 3:
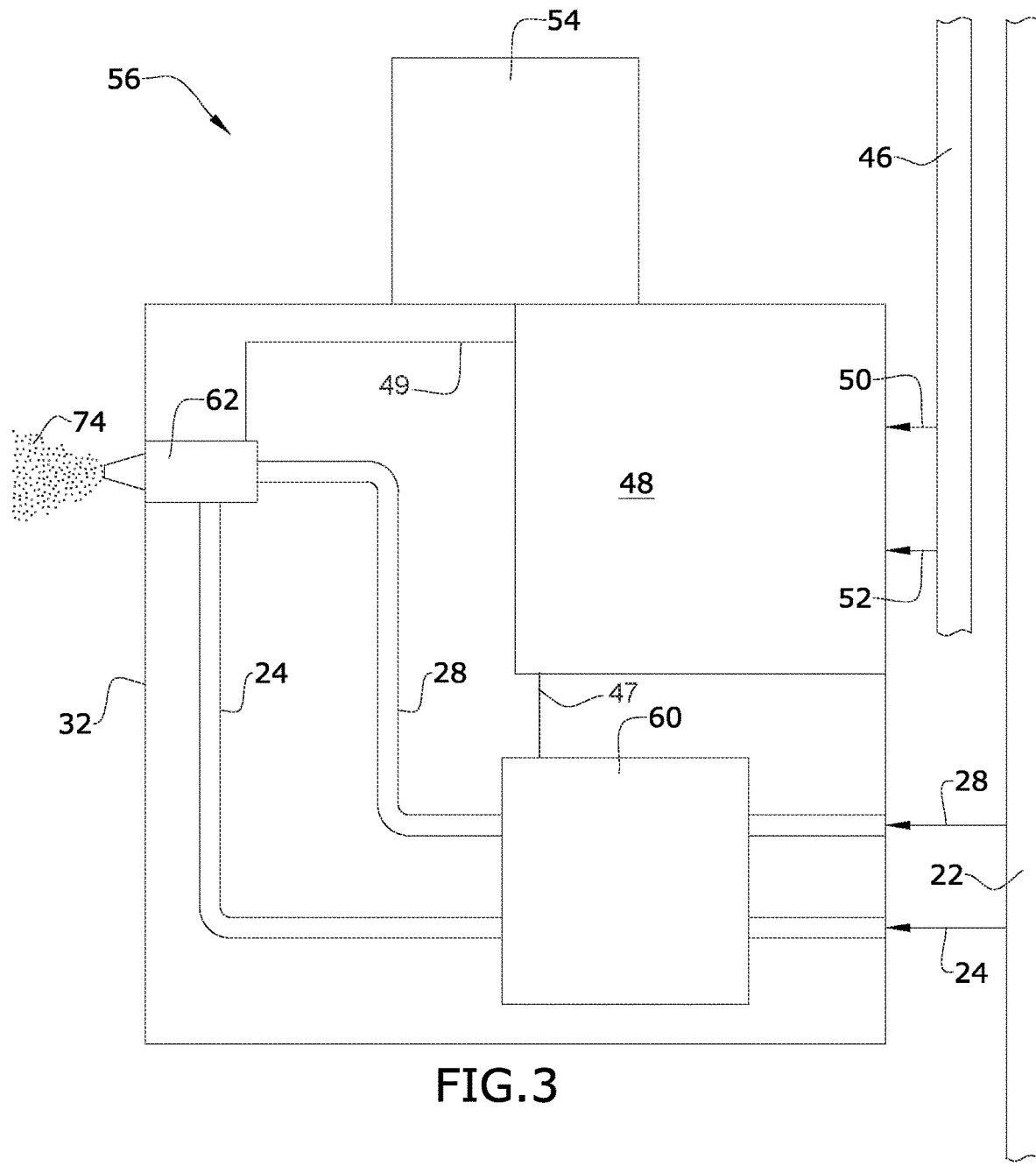
FIG. 3 is a schematic view of a snow module thereof.

Referring to FIGS. 1 through 3, FIG. 1 shows a system area, enclosure, or room 10 and an attendee area or room 68. As shown, the system area 10 contains an air compressor 12, a haze fluid reservoir 14 with a first pump 16, a snow fluid reservoir 18 with a second pump 20, and a control system or controller 66. The control system 66 electrically communicates with the air compressor 12, the first pump 16, and the second pump 20 by way of control and power line bundles 46. When activated by the control system, the first pump 16 selectively delivers haze fluid via haze fluid lines 26 to a plurality of haze modules 30 mounted in the attendee area 68 ceiling 76, the second pump selectively delivers snow fluid via snow fluid lines 28 to a plurality of snow modules 56 mounted in the attendee area 68 ceiling 76, and the air compressor 12 selectively delivers compressed air via compressed air lines 24 to the haze modules 30 and/or the snow modules 56. The compressed air lines 24, the haze fluid lines 26, and the snow fluid lines 28 are bundled in hoses 22 from the system area 10 to the attendee area 68. The control system 66 also electrically communicates with the haze modules 30 and the snow modules 56 via control and power line bundles 46. The attendee area 68 may be treated by fog haze 72 and/or artificial snow 74 delivered above the attendees 70. Reservoir return lines 64 return unused compressed air, unused haze fluid, and unused snow fluid to the system area 10.

A haze module 30 is shown in more detail in FIG. 2. A haze fluid line 26 bundled with a compressed air line 24 in a hose 22 deliver haze fluid 34 and compressed air to a casing or housing 32 mounted to the ceiling 76 with mounting hardware 54. The fluid 34 flow is controlled by a control module 48 connected by a control line 49 to a valve 36 housed within the housing 32 which is coupled with and feeds a fill tube 38 to maintain a predetermined fluid level monitored by a fluid level sensor 39. The compressed air is bubbled into the fluid 34 by way of an air nozzle 40 to produce a fog haze 72, which exits through an aperture or opening 44 in the housing 32 sidewall after rising vertically past a baffle 42 in the housing 32. The haze module 30 is operated by the control and power circuitry box or assembly 48 which receives fluid level sensor input 51 as well as control inputs 50 and power inputs 52 from the control system 66 via the control and power line bundles 46.

A snow module 56 is shown in more detail in FIG. 3. A snow fluid line 28 bundled with a compressed air line 24 in a hose 22 deliver snow fluid and compressed air to a valve 60 within a casing or housing 32 mounted to the ceiling 76 with mounting hardware 54. The snow module 56 is operated by a control module 48, i.e., a control and power circuitry box, which receives control inputs 50 and power inputs 52 from the control system 66 via the control and power line bundles 46. The control module 48 controls the valve 60 via control line 47 which feeds compressed air and snow fluid to a diffuser 62 which produces and releases artificial snow 74. The control module 48 also controls the diffuser 62 via control line 49.

It should be understood, of course, that the foregoing relates to exemplary embodiments of the invention and that modifications may be made without departing from the spirit and scope of the invention as set forth in the following claims.

What is claimed is:

1. A modular anti-microbial aerosol atmospheric effect delivery system, comprising:
   an air compressor in a system enclosure;
   a haze solution reservoir in the system enclosure;

an artificial snow solution reservoir in the system enclosure;

an electronically controlled haze module mounted above an attendee room; and an electronically controlled artificial snow module mounted above the attendee room;

wherein said electronically controlled haze module fluidly communicates with the air compressor and the haze solution reservoir by way of a hose system and said electronically controlled artificial snow module fluidly communicates with the air compressor and the artificial snow solution reservoir by way of the hose system.

2. The modular anti-microbial aerosol atmospheric effect delivery system of claim 1, wherein the electronically controlled haze module is one of a plurality of electronically controlled haze modules and the electronically controlled artificial snow module is one of a plurality of electronically controlled artificial snow modules.

3. The modular anti-microbial aerosol atmospheric effect delivery system of claim 1, further comprising a reservoir return line fluidly communicating the electronically controlled haze module and the electronically controlled artificial snow module with the system enclosure.

4. The modular anti-microbial aerosol atmospheric effect delivery system of claim 1, wherein the haze solution reservoir is coupled with the hose system by way of a first pump and the artificial snow solution reservoir is coupled with the hose system by way of a second pump.

5. The modular anti-microbial aerosol atmospheric effect delivery system of claim 4, further comprising a controller electrically communicating with the air compressor, the first pump, the second pump, the electronically controlled haze module, and the electronically controlled artificial snow module by way of control and power line bundles.

6. The modular anti-microbial aerosol atmospheric effect delivery system of claim 5, wherein the electronically controlled haze module further comprises:

a housing mounted to a ceiling with mounting hardware, said housing having a baffle on a sidewall thereof and an aperture formed in the sidewall vertically above the baffle;

an electronically controlled valve coupled with a fill tube housed within the housing and fluidly communicating with the haze solution reservoir by way of the hose system;

an air nozzle housed within the housing and fluidly communicating with the air compressor by way of the hose system, said air nozzle extending below a predetermined fluid level;

a fluid level sensor housed within the housing, said fluid level sensor extending below the predetermined fluid level; and a control and power circuitry assembly housed within the housing and electrically communicating with the fluid level sensor, the electronically controlled valve, and with the controller.

7. The modular anti-microbial aerosol atmospheric effect delivery system of claim 5, wherein the electronically controlled artificial snow module comprises;

a housing mounted to a ceiling with mounting hardware;

an electronically controlled valve housed within the housing and fluidly communicating with the artificial snow solution reservoir and the air compressor by way of the hose system;

a diffuser mounted on a sidewall of the housing and coupled with the electronically controlled valve; and a control and power circuitry assembly electrically communicating with the controller and the electronically controlled valve.

8. Aerosol anti-microbial atmospheric effect compositions, comprising:

(a) an artificial snow solution including sodium lauryl sulfate and citric acid; and (b) a haze solution including an alkene glycol and at least one anti-microbial component selected from the group consisting of hydrogen peroxide and citric acid.

9. The aerosol anti-microbial atmospheric effect compositions of claim 8, further comprising compressed air, wherein the artificial snow solution and the haze solution are aerosols formed by the compressed air.

10. An atmospheric effect delivery method of disinfecting an inhabited room, comprising:

(a) providing the modular anti-microbial aerosol atmospheric effect delivery system of claim 1;

(b) providing an artificial snow solution including sodium lauryl sulfate and citric acid in the artificial snow solution reservoir;

(c) providing a haze solution including an alkene glycol and at least one anti-microbial component selected from the group consisting of hydrogen peroxide and citric acid in the haze solution reservoir;

(d) delivering the haze solution and compressed air to the electronically controlled haze module;

(e) delivering the artificial snow solution and the compressed air to the electronically controlled artificial snow module;

(f) continuously operating the electronically controlled haze module; and (g) intermittently operating the electronically controlled artificial snow module.

\* \* \* \* \*